(12) United States Patent
Czaja et al.

(10) Patent No.: US 8,725,291 B2
(45) Date of Patent: May 13, 2014

(54) METHOD AND APPARATUS FOR REMOTE MONITORING OF DAILY DISPENSING OF MEDICATION

(75) Inventors: Stanislaw Czaja, Cardiff by the Sea, CA (US); William Welch, Cardiff by the Sea, CA (US); Ilona Stawski, Avon Lake, OH (US); Cory Marqusee, Cardiff by the Sea, CA (US)

(73) Assignee: IPComm, Cardiff, CA (US)

( * ) Notice: Subject to any disclaimer, the term of this patent is extended or adjusted under 35 U.S.C. 154(b) by 194 days.

(21) Appl. No.: 12/853,511

(22) Filed: Sep. 13, 2010

(65) Prior Publication Data
US 2012/0065776 A1    Mar. 15, 2012

(51) Int. Cl.
*G06F 17/00*      (2006.01)

(52) U.S. Cl.
USPC ............................. 700/240; 700/237; 700/244

(58) Field of Classification Search
USPC .......................................... 700/237, 240, 244
See application file for complete search history.

(56) References Cited

U.S. PATENT DOCUMENTS

| | | | |
|---|---|---|---|
| 5,408,443 A * | 4/1995 | Weinberger | 221/3 |
| 6,539,281 B2 * | 3/2003 | Wan et al. | 700/236 |
| 6,550,618 B2 | 4/2003 | Peterson | |
| 7,359,765 B2 | 4/2008 | Varvarelis et al. | |
| 7,366,675 B1 * | 4/2008 | Walker et al. | 705/2 |
| 7,543,718 B2 | 6/2009 | Simon | |
| 7,584,849 B2 | 9/2009 | Mauk | |
| 7,612,662 B2 | 11/2009 | Niemiec et al. | |
| 7,621,231 B2 | 11/2009 | McNeely | |
| 7,639,120 B2 | 12/2009 | Sekura | |
| 7,711,449 B2 | 5/2010 | Abdulhay et al. | |
| 7,713,238 B2 | 5/2010 | Mernoe | |
| 7,755,478 B2 * | 7/2010 | Niemiec et al. | 700/244 |
| 7,885,725 B2 * | 2/2011 | Dunn | 700/237 |
| 7,978,564 B2 * | 7/2011 | De La Huerga | 700/242 |
| 8,108,068 B1 * | 1/2012 | Boucher et al. | 700/236 |
| 8,195,330 B2 * | 6/2012 | Coe | 700/243 |
| 2009/0301925 A1 | 12/2009 | Alloro et al. | |
| 2009/0315702 A1 * | 12/2009 | Cohen Alloro et al. | 700/240 |

OTHER PUBLICATIONS

ORCATHECH Living Laboratory, "Smart Pillbox", AARP.org Bulletin, Apr. 2012, p. 16.
E-PILL, LLC Medication Reminders, 3 pages from catalogue, downloaded by Applicant on Dec. 6, 2012.
E-PILL, LLC Medication Reminders, 2 pages from catalogue, downloaded by Applicant on Dec. 6, 2012.

* cited by examiner

*Primary Examiner* — Timothy Waggoner

(57) ABSTRACT

A method and apparatus for remote monitoring of daily dispensing of medication is disclosed. In one embodiment, a dispensing unit, equipped with a weight sensing mechanism, such as scale or balance, communicates with a monitoring application residing in a wireless terminal. The monitoring application provides supervision over a medication dispensing process.

13 Claims, 5 Drawing Sheets

METHOD AND APPARATUS FOR REMOTE MONITORING OF DAILY DISPENSING OF MEDICATION

FIELD OF THE INVENTION

The present invention relates to the field of wireless health Monitoring system, specifically to the monitoring of daily dispensing of medications.

DESCRIPTION OF THE RELATED ART

As the national health care systems cope with the increasing cost of care for the growing number of patients with chronic diseases, or an elderly requiring a daily dose of medication to sustain their quality of life, there is a need for a low cost, low maintenance monitoring system that insures that the patient actually remembered to take his/her daily dose of medication at the correct time.

In recent years, the use of mobile devices and, in particular, cellular telephones has proliferated. As a result, cellular telephones or other wireless devices, installed in primary residences, are considered as candidates to provide various health care-monitoring and even health care-delivering functions.

Considering that strict adherence to the timely dispensing of medication is critical to the quality of provided health care, combining of simple dispensing mechanism with the ubiquitous cellular phone can provide the benefits of virtual medical supervision of the medication dispensing regime at very low cost.

Many medication dispensing methods were proposed in the past—from very simple containers with daily compartments and a textual information cards, through programmable dispensing systems, to complex systems intended for centralized dispensing in hospitals. However, none of these systems provides a quality of medical supervision at costs applicable for personal use.

Most dispensing systems intended for a personal use consist of a daily, weekly, etc. containers and textual information card describing dosage to be dispensed at each dispensing period. Sometimes the supplied information card allows the patient to enter "reminder" information. While previous devices provide some form of organized dispensing for personal use, they lack the ability to verify usage and/or to allow intervention should usage not occur or be inaccurate. Example of previously described systems may be found in: U.S. Pat. Nos. 6,550,618 and 7,584,849 and 7,543,718 and 7,621,231

Another type of a medicine dispensing system intended for a personal use consists of a programmable device capable of time-tracking and reminding the patient when to next take their medication. Such devices provide some enforcement of medication regime, but their capability is limited to a simple audio or visual reminder They are unable to inform external medical supervisors of medication compliance or are unable to receive instructions from a remote medical supervisor. Examples of such systems may be found in: U.S. Pat. Nos. 7,639,120 and 7,359,765.

Another type of medicine dispensing system embeds some supervisory function either in the medication packaging, such as in U.S. Pat. No. 7,612,662 or U.S. patent application No. 2009/0301925, or rely on complicated electromechanical system where each type of the medication (pill) resides in a separate container with the dispensing from those multiple containers controlled by the micro-processor, such as in U.S. Pat. No. 7,711,449, or an electromechanical pill dispenser such as describe in U.S. Pat. No. 7,713,238. A common problem of these systems is their reliance on new packaging technology (e.g. inclusion of RFID into every package, while providing no solution for multi-pill containers), or proposing complicated electromechanical dispensers unable to hold different size(s) of the medication. Moreover, none of these devices provide feedback or other important information to the medical supervisor regarding patient compliance of medication consumption.

SUMMARY OF THE INVENTION

This invention allows for the remote monitoring of the daily dispensing of prescription drugs by at-home care, an elderly patient or a clinical trial patient. The system consists of a dispensing unit equipped with sensor(s), a monitoring application and a wireless terminal, such as a cell-phone providing access to the Internet. The monitoring application and wireless Wide Area Network (WAN) modem can reside within the dispensing unit or alternatively, the dispensing unit can communicate with the application residing in the user/patient cell phone over suitable RF interface, such as Bluetooth, etc.

The proposed invention integrates a simple medication dispensing container similar to one well known from prior art with a sensitive weighting mechanism in the form of a scale or balance, or Microelectromechanical System (MEMS) sensor (s) interfacing over a short range wireless link similar to Bluetooth with the medicine dispensing application residing in the patient's cell phone.

Such a system can provide real-time monitoring of medication compliance by alerting the user when the next set of medication should be taken. In addition the dispenser can sense the removal of the medication via weight change and thereby help to confirm compliance of the dispersion of the medication. Furthermore, if the medication is not dispensed at the prescribed time, such a system may provide a local alert to the patient and if no dispensing is again verified, a remote alerts a list of patient medical supervisors (family, friends, physicians, etc) that medication compliance has not been confirmed.

Furthermore, if such system is equipped with additional monitoring sensors such as: heart rate, blood pressure, glucose level, etc, it can provide close-loop monitoring of the patient's response to the drug delivery, thereby allowing a physician to change the medication when a negative response (or no response) to the prescribed drug has been detected. Beside compliance verification, the cell-phone based application guarantees a continuous and secure connection with clinical and family supervisors, thereby providing low cost and reliable patient care. Such a monitoring system can operate using any of wireless WAN technology such as: cdma2000 (1xRTT and EV-DO), UMTS, LTE, WiMax, etc.

Various embodiments for a method for monitoring the daily dispensing of medication are presented.

In one embodiment, the method may include a daily medication container integrated with a scale or balance which is capable of measuring the weight of dispensed medication and an integrated wireless Persona Area Network (PAN) such as Bluetooth which interfaces with the monitoring application residing in the patient's cellular phone.

In some embodiments, the daily medication container is a separate container of any sort which can be placed on a scale or balance which is capable of measuring weight of dispensed medication integrated with PAN wireless network such as Bluetooth which interfaces with the monitoring application residing in the patient's cellular phone. In such embodiment the cell phone based application must be able to calibrate weight (and subsequent changes over time) of the medication container.

In another embodiment, the daily medication container is equipped with MEMS sensors capable of detecting the dispensing of the medication either by measuring the change of the weight, before and after dispensing, and communicate over the integrated PAN wireless network such as Bluetooth with the monitoring application residing in the patient's cellular phone.

In all of these embodiments, the monitoring application performs all the functions related to patient and medical supervisor authentication, calibration of medication containers and medication, supervision of dispensing time and medication quantity including alerts and notification to the user/patient, "book-keeping" of the dispense medication, scheduling of the next dispensing time, and in case of detected non-conformance to the prescribed dispensing regime executes local and remote alarms to other interested third parties.

Furthermore, when the application is augmented with additional sensors capable of monitoring specific bio-functions such as: pulse, heart rate, arrhythmia, blood pressure, etc. monitors, the proposed method may provide near-real-time feedback about the effects of the medication to the supervising medical professional.

BRIEF DESCRIPTION OF THE DRAWINGS

A better understanding of the present invention can be obtained when the following detailed description of the preferred embodiment is considered in conjunction with the following drawings, in which.

Figure 1:
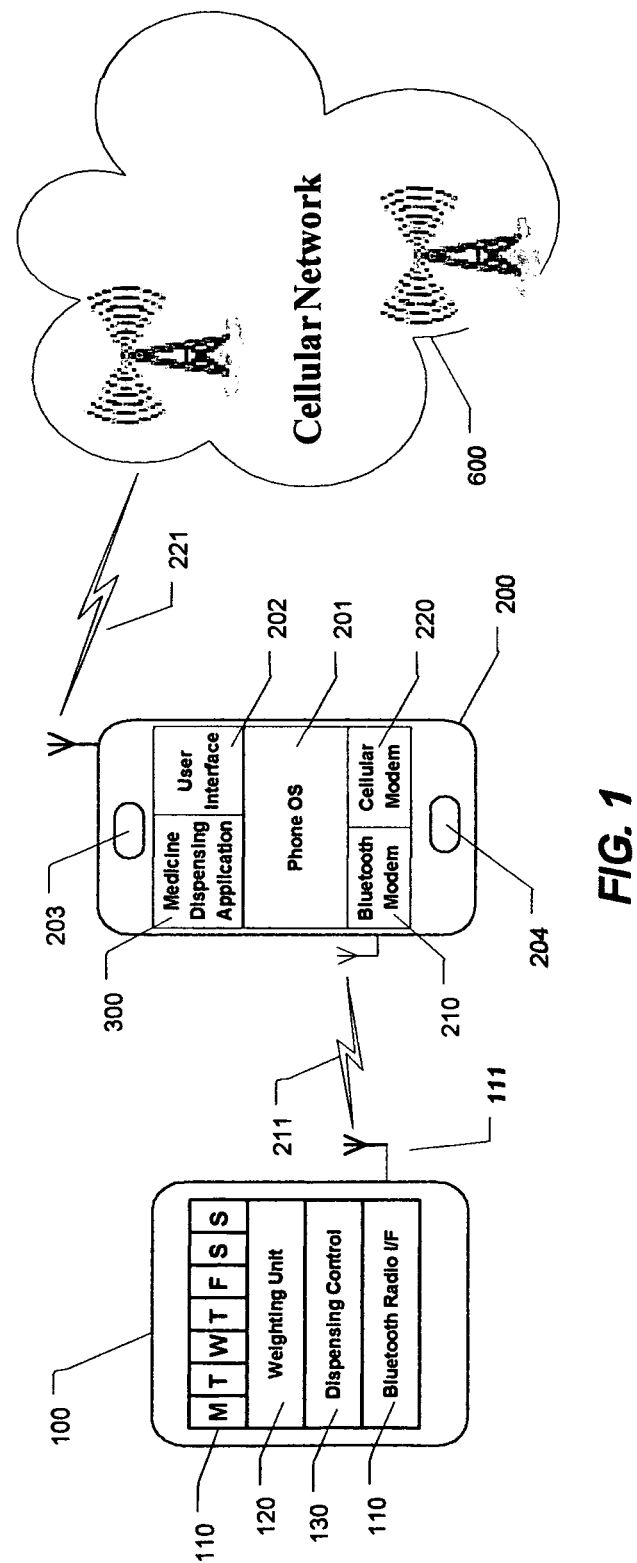
FIG. 1 is an exemplary medicine dispensing compliance system according to one embodiment.

While the invention is susceptible to various modifications and alternative forms, specific embodiments thereof are shown by way of example in the drawings and are herein described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The following is a glossary of terms used in the present application:

Memory Medium—Any of various types of memory devices or storage devices. The term "memory medium" is intended to include an installation medium, e.g., a CD-ROM, floppy disks 104, or tape device; a computer system memory or random access memory such as DRAM, DDR RAM, SRAM, EDO RAM, etc.; or a non-volatile memory such as a magnetic media, e.g., a hard drive, or optical storage. The memory medium may comprise other types of memory as well, or combinations thereof. In addition, the memory medium may be located in a first processor in which the programs are executed, or may be located in a second different processor which connects to the first processor over a network, such as wireless PAN or WAN network or the Internet. In the latter instance, the second processor may provide program instructions to the first processor for execution. The term "memory medium" may include two or more memory mediums which may reside in different locations, e.g., in different processors that are connected over a network.

Application—the term "application" is intended to have the full breadth of its ordinary meaning. The term "application" includes: 1) a software program which may be stored in a memory and is executable by a processor; or 2) a hardware configuration program useable for configuring a programmable hardware element.

Software Program—the term "software program" is intended to have the full breadth of its ordinary meaning, and includes any type of program instructions, code, script and/or data, or combinations thereof, that may be stored in a memory medium and executed by a processor. Exemplary software programs include programs written in text-based programming languages, such as C, C++, Visual C, Java, assembly language, etc.; graphical programs (programs written in graphical programming languages); assembly language programs; programs that have been compiled to machine language; scripts; and other types of executable software. A software program may comprise two or more software programs that interoperate in some manner.

Computer System—any of various types of computing or processing systems, including cell phone, personal computer system (PC), mainframe computer system, workstation, network appliance, Internet appliance, personal digital assistant (PDA), television system, grid computing system, or other device or combinations of devices. In general, the term "computer system" can be broadly defined to encompass any device (or combination of devices) having at least one processor that executes instructions from a memory medium.

Medical Supervisor—in the context of this invention, any person authorized to enter or modify dispensing operational parameters, receive remote alarms, notification or transmission of monitored data. This person may be a family member or trained medical personnel.

Patient—in the context of this invention, person supervised by the medicine dispensing application.

Description Of Preferred Embodiment

The proposed method leverages on the properties of wireless Personal Area Network (PAN) such as Bluetooth and wireless Wide Area Network (WAN), such as a cell-phone, and combines the inherent benefits provided by those networks with the medicine dispensing device which may take the form of a simple multi-compartment container, where the compartment are labeled with the day-of-the-week and a weighting station, capable of detecting when the medications are removed and able to communicate with the cell-phone based monitoring application over short range wireless link similar to Bluetooth Assuming that both the precise weight of the dispensing container and the single dosage of medication is known and calibrated, and the total number of individual doses in the container is known, one can determine if a single dosage of medication was dispensed by measuring the total weight of the dispenser containing medication before and after dispensing.

Such dispenser and associated weighting device is equipped with a PAN wireless communication link, such as Bluetooth. The device is controlled over this said PAN communication link by the Dispensing Application control software residing in the cell-phone which in turn is connected to the wireless WAN and consequently to the Internet. In this fashion one may provide a reliable remote medication dispense monitoring system.

In such a system the intelligence and supervision is embedded in the medication dispensing application software residing in the user/patient cell-phone. This application is able to determine the time and dosage which needs to be dispense, alert the user/patient of the need to dispense medication, verify the correct amount of medication was dispensed, and if not dispensed then alert the user. In the case that this alert provides no verifiable results, additional alerts will then be extended to "medical supervisors" or other interested third parties thereby alerting important others that medical compliance has not been achieved.

Figure 2:
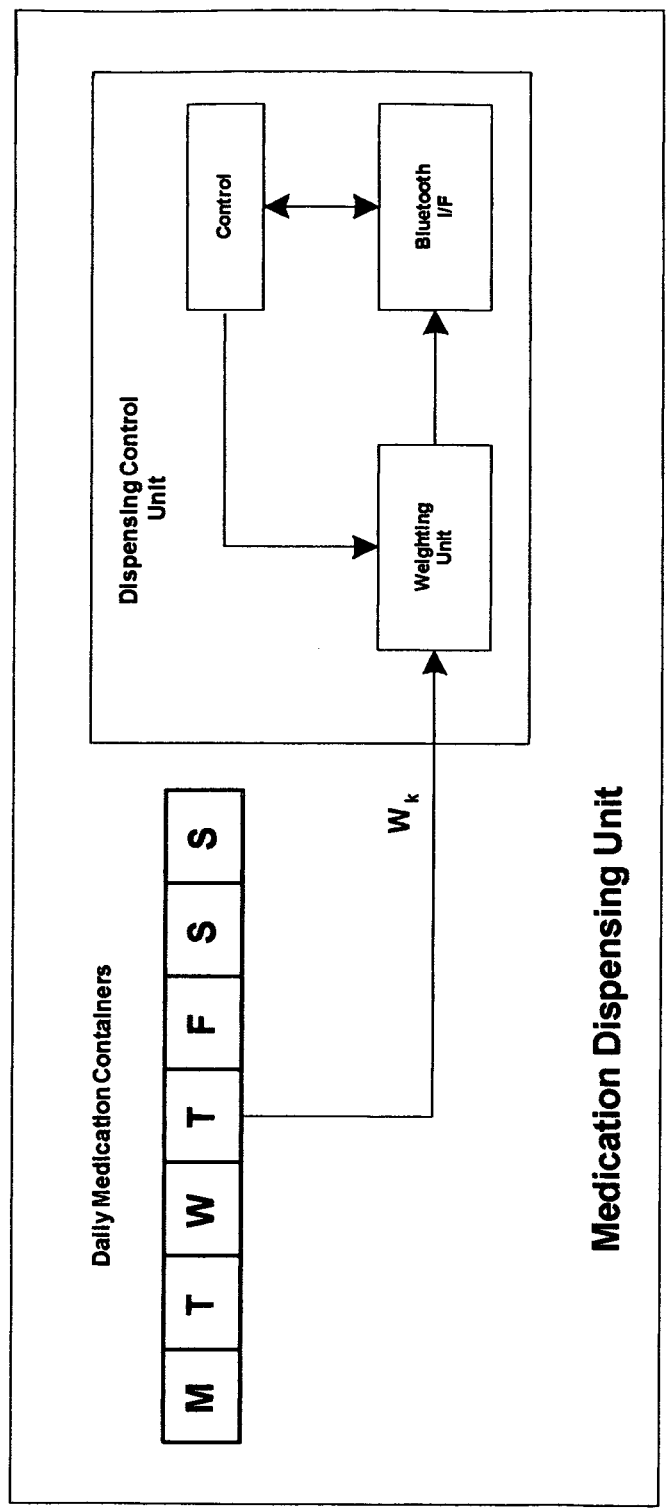
FIG. 2 is an exemplary block diagram of the medicine dispensing unit.
Figure 3:
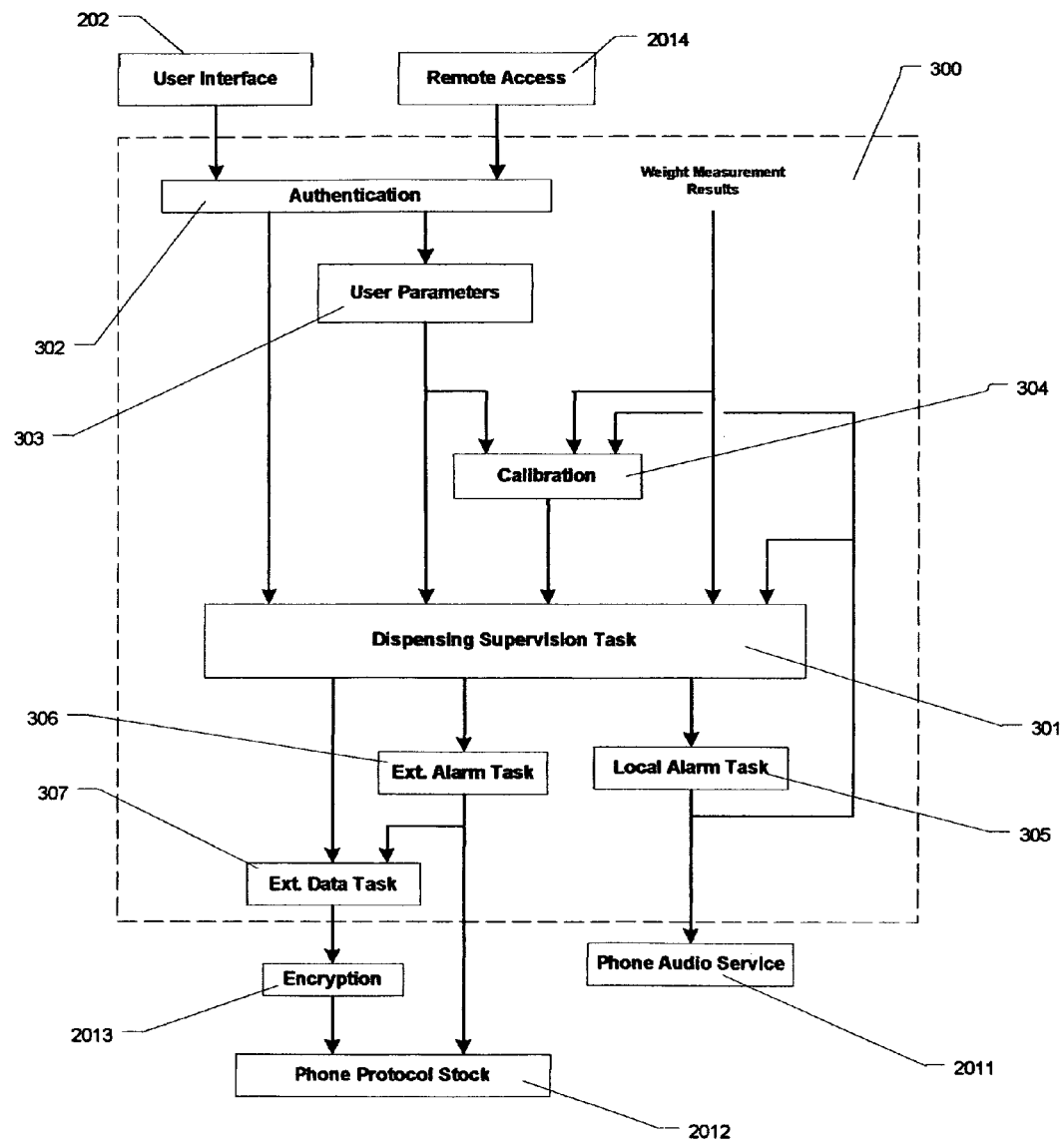
FIG. 3 is a flowchart of an exemplary method for processing of the cell-phone based medicine dispensing application.

This invention integrates wireless access technology with a simple dispensing unit to provide reliable remote medication compliance system without constant supervision by a health professional or family member. An example of such system is presented in FIG. 1 and FIG. 2.

The medicine dispensing unit 100 consisting of a weekly medication container 110, where each compartment is dedicated for a single day (dosage) of the medications, a weighting unit 120 capable of measuring the weight of the dispensed medication, a dispense unit control program 130 in form of stand-alone software of integrated into radio interface Media Access layer (MAC) functionality, and a PAN wireless interface 140 in form of Bluetooth, etc. communicating over the 141 RF link with the application.

The medicine dispensing application 300 resides inside the wireless phone 200 program memory and is under general control of phone Operating System (OS) 201 and communicates with the dispensing unit 100 over the phone Bluetooth modem 210 and with the wireless WAN network over the cellular modem 200 and RF 221. Furthermore, the medicine dispensing application interface with the phone user through the phone User Interface (UI) 202, speaker 203 and microphone 204.

The wireless phone (also referred to as access terminals) 200 may include any type of device which may be used in a cellular network, e.g., RF communication. Mobile devices 200 may include cellular (or cell) phones (including smart phones), personal digital assistants (PDAs) with mobile communication capabilities, laptops or computer systems with mobile communication components, and/or any device which is operable to communicate with a cellular network. The mobile devices may use various different protocols, e.g., cdma2000 (1xRTT and EV-DO), UMTS, LTE, WiMax, or others).

The user parameters 303 of the medication dispensing application 300 may be entered/modified after authentication 302 by the user and or medical supervisors, locally through the UI 202, or remotely through the WAN radio interface 2011.

The first information 3031 of the user parameters 303 may will include identity information of the authorized user and medical supervision personnel and/or a plurality of parameters which describe various aspects of the accessing the remote medical supervisors. For example, the plurality of parameters may indicate phone numbers or IP addresses of medical supervisors, type of information to be sent to selected supervisor, etc.

The second information 3032 may include exact weight of each individual medication to be dispensed and a specific action if one of the prescribed medication was not dispensed. As well as requesting monitoring of specific bio-functions, such as heart rate, blood pressure, etc. at the specified interval after medication was dispensed.

The third information 3033 may include the dispensing schedule and more specifically the time and the weight of medication to be dispensed at each predefined period. Additionally, the third information may contain the amount of time application will wait for the response of various devices, i.e. wake-up time of the dispensing unit, or response to various local alerts and external alarms.

The fourth information 3034 may contain a list of valid responses pre-approved by the medical supervisor to allow cancellation of local alerts. Those valid responses may be selected from the generic list by the medical supervisor.

The fifth information 3035 may contain the type of local alerts and the actions the monitoring application must take in such cases. More specifically, it may contain the selection of one or more of the predefined audio and/or textual messages intended to alert the user/patient about the next medication dispensing or in case such dispensing didn't occurred or if the dispensing amount was different from the scheduled one or in the case the total medication weight before dispensing was not equal to the weight stored after the previous dispensing.

The six information 3036 may contain the type of remote alarms and the actions the monitoring application must take in such cases. More specifically, it may contain the selection of one or more of the predefined audio and/or textual messages intended to alert the patient medical supervisor about the discrepancy in medication dispensing or in case medication dispensing didn't occur, or if the dispensing amount was different from the scheduled one or in the case the total medication weight before dispensing was not equal to the weight stored after the previous dispensing and the local alert was not canceled by the user/patient corrective action.

Information contained within the user parameters 303 are used as an operational parameters by the dispensing supervision task 301 and some in the calibration process 304.

Figure 4:
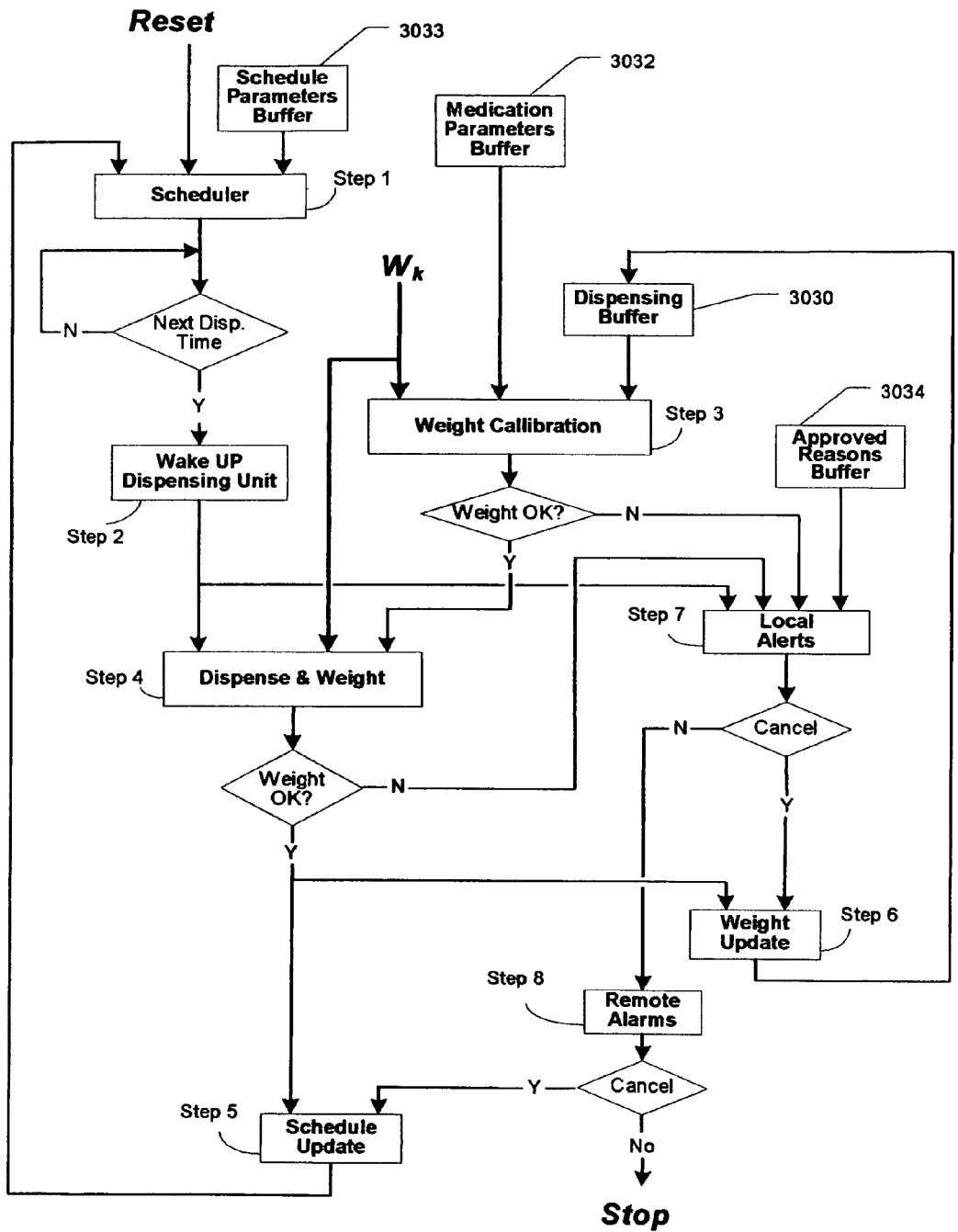
FIG. 4 is a flowchart of an exemplary method of the supervisory process of the exemplary medicine dispensing application.

In Step 1 of FIG. 4 after the RESET, the Scheduler programs all appropriate timers with the values defined by the third information 3033, then start the application. When the next dispense interval arrives, application enters Step 3 to wake-up the dispensing unit by sending appropriate commands over the PAN wireless interface, then enters Steps 4 waiting for medication dispensing and Step 7 to alert patient about the incoming medication period.

In Step 4, when the weighting unit of the dispenser is READY, the application retrieves user parameters stored in second information 3032, the weight values stored in Dispensing Buffer 3030 after the previous dispense, and compare those values with the current wait measurement $W_k$ received from the weighting unit.

If the calibrated weight obtained in Step 3 is within the limit of the current dispensing cycle, the dispensing application enters Step 4 and waits for a length of time specified in the third information 3033 then records the dispensing.

However, if the calibrated weight is different than the one retrieved form the Dispensing Buffer 3030 after the previous dispensing period, the application enters into Step 7 and issues local alerts. Application will stay in Step 7 until the local alert is canceled or until the time stored in third information 3033 elapses. Local alarms may be in the form of predefined audio or textual messages.

In response to local alarm, a patient may select on of the entries from the list of valid reasons pre-approved by the medical supervisor and stored in Approved Reasons Buffer 3034. One entry in such list may be patient's need to take some of the medication ahead of time due to his/her condition, another may be the patient's schedule conflict, yet another may be a recent directive by the medical personnel. If a valid reason for such discrepancy was received, the new weight value is calculated in Step 6, the Dispensing Buffer 3030 is updated and the dispensing process may continue to Step 4.

Local alerts and the pre-approved reason for temporary deviations in the amount (weight) of medication to be dispensed in the current dispensing period allows for emergency dispensing as well as recovery from minor patient or system errors, such as: out of RF coverage area; battery power down, etc. while still providing high reliability and minimizing unnecessary external alarms.

If the local alert is not cancelled within the period of time defined in third information 3033, the application enters Step 8 and sends an external alarm to the predefined recipients over the cellular network. Such external alarm may have a form of predefined SMS, or voice messages or patient related data.

After external alarm is sent, application waits for the intervention from the medical supervisor, which will cancel such alarm. To cancel the alarm, the medical supervisor must log into the application using either phone UI 202 or remotely using API interface 2011 (remote access if such functionality is provided or command embedded in the SMS message), after appropriate authentication. If such intervention is not received within the time period specified in third information 3033, the application goes to the STOP state, from which it can only recover after RESET provided of by the medical supervisor.

When application is in Step 4 and the change in the dispensing container weight was detected, and the dispensing weight change is equal to the predefined dosage, the dispensing application subtracts the weight of the current dispense from the previous container weight and through Step 6 updates the Dispensing Buffer which then is used as the calibration value for the next dispensing period. Additionally, through the Step 5 it updates the Scheduler and instructs the dispensing unit to enter low-power or SLEEP mode.

When application is in Step 4 and the change in the dispensing container weight was detected, and the weight change is not equal to the predefined dosage weight, the dispensing application enters Step 7 to alert the patient. In response to the local alarm, the patient may select one of the entries from the list of valid reasons pre-approved by the medical supervisor and stored in Approved Reasons Buffer 3034.

If this local alert is not cancelled within the period of time specified in third information 3033, application enter Step 8 sending an external alarm to the predefined recipients over the cellular network. Such external alarm may have a form of predefined SMS, or voice messages, or patient related data. After external alarm is sent, application waits for the intervention from the medical supervisor, which will cancel such alarm. To cancel such alarm the medical supervisor must log into the application using either phone UI 202 or remotely using API interface 2011 (remote access if such functionality is provided or command embedded in the SMS message), after appropriate authentication. If such intervention is not received within the time period specified in third information 3033, the application goes to the STOP state, from which it can only recover after RESET provided of by the medical supervisor.

Depending on the type of the dispensing container design, the dispensing application may instruct the container to open the "current" compartment, or wait for an ACCEPT command from a dedicated unit interface (i.e. push-button), or simply monitor the change in the weight of the dispensing container.

Figure 5:
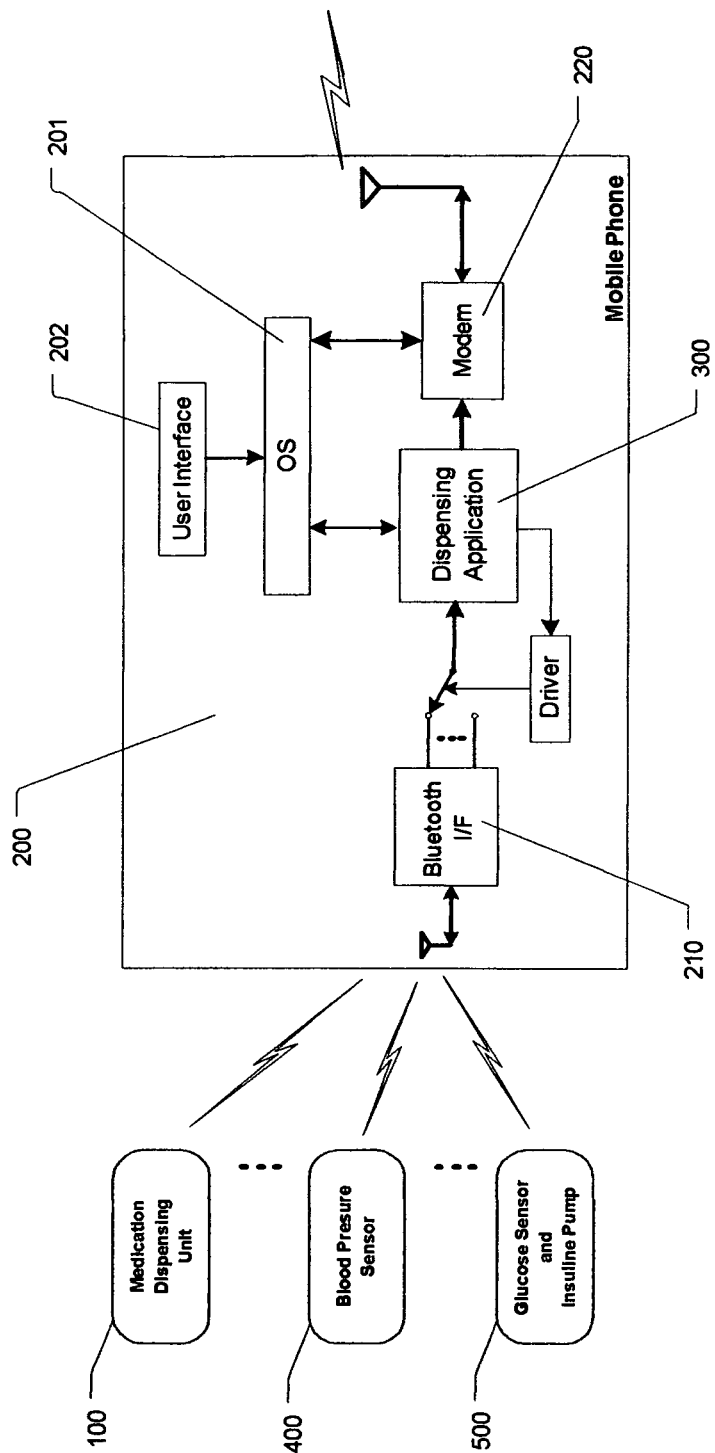
FIG. 5 is a block diagram of the medicine dispensing and analysis system

When the application 300 of FIG. 5 includes additional monitoring functionality to support monitoring of various bio-function, such as: blood pressure 400; glucose level sensor 500, heart rate/arrhythmia sensor, etc. it can provide real-time feedback to the medical personnel regarding patient's reaction to medication.

In such case, at the predefined time for medication dispensing, and after alerting the patient in step 2 and calibration procedures in step 3 application 300 performs all normal procedures specified for the current dispense period. Then it enters in the Medication Response Monitoring mod, in which depending on the parameters stored in the second information 3032 and the third information 3033 it will perform monitoring of specified bio-functions. The results of such measurements may be store in the local RAM or sent to the medical supervisor.

In case patients related data are to be sent to the external destination, the application task 307 formats the data records then using encryption service 2013 sends data to the cellular modem for transmission over the WAN wireless network.

We claim:

1. A medicine dispensing compliance system, the dispensing system comprising:
 a medicine dispensing unit; and
 a medicine dispensing application, in wireless communication with the medicine dispensing unit,
wherein the medicine dispensing unit includes a medication container, a weighting unit, a dispensing control mechanism, and a wireless communication interface; and wherein the medicine dispensing application includes a user interface adapted to interface with a selected user of the medicine dispensing compliance system, and wherein the medicine dispensing application further includes a plurality of user parameters associated with and corresponding to the selected user; and wherein the plurality of user parameters include at least one of the following parameters; identity information related to the selected user; dispensing scheduling information including a desired weight of medicine to be dispensed at a pre-defined period of time; a list of pre-approved alert cancellation responses; a plurality of local alerts issued by the dispensing application; and a plurality of actions to be taken by the dispensing application under selected conditions, wherein the medication container comprises a weekly medication container including individual compartments associated and corresponding to a single day dosage of medicine to be taken by the selected user.

2. The medicine dispensing system of claim 1, wherein the weighting unit outputs a current weight measurement Wk of medicine currently contained in the medication container.

3. The medicine dispensing system of claim 1, wherein the wireless communication interface comprises a cellular telephone interface.

4. The medicine dispensing system of claim 1, wherein the wireless communication interface comprises a Bluetooth radio interface.

5. The medicine dispensing system of claim 1, further comprising a cellular telephone in wireless communication with a cellular network, wherein the cellular telephone includes at least one processor, and wherein the medicine dispensing application comprises a software program executed by the at least one processor.

6. The medicine dispensing system of claim 5, wherein the cellular telephone comprises a smart phone.

7. The medicine dispensing system of claim 5, wherein the cellular telephone includes a Bluetooth radio interface in wireless communication with the wireless communication interface of the medicine dispensing unit.

8. The medicine dispensing system of claim 1, wherein the weighting unit comprises a sensitive weighting system.

9. The medicine dispensing system of claim 1, wherein the weighting unit comprises a balance or scale.

10. The medicine dispensing system of claim 1, wherein the medication container is integrated with the wireless communication interface and the weighting unit.

11. The medicine dispensing system of claim 1, wherein the medication container is separate from the wireless communication interface and the weighting unit.

12. The medicine dispensing system of claim 1, wherein the medicine dispensing application performs all of the following medicine dispensing functions: authentication of the selected user and a plurality of selected medical supervisors; scheduling of dispensing time intervals according to one or more scheduling parameters; alerting the selected user of an incoming dispensing period by means of audio or textual messages; calibration of the medication container and of the medicine dispensed at the pre-defined period of time; measuring a weight of the medicine dispensed at the pre-defined period of time and comparing the measured weight with the desired weight; alerting the selected user when the measured weight varies substantially from the desired weight; alarming the selected medical supervisors if the dispensing time period is missed, or if the measured weight varies substantially from the desired weight; and canceling the alarming function if a pre-defined set of conditions are met.

13. The medicine dispensing system of claim 1, wherein the medicine dispensing application includes all of the user parameters defined in claim 1.

\* \* \* \* \*